United States Patent [19]
Fischer et al.

[11] Patent Number: 5,877,152
[45] Date of Patent: Mar. 2, 1999

[54] METHOD FOR ISOLATION OF HIGHLY PURE VON WILLEBRAND FACTOR

[75] Inventors: Bernhard Fischer, Vienna; Artur Mitterer, Orth/Donau; Friedrich Dorner, Vienna; Hans-Peter Schwarz, Vienna; Peter Turecek, Vienna; Johann Eibl, Vienna; Falko-Guenter Falkner; Uwe Schlokat, both of Orth/Donau; Wolfgang Mundt, Vienna; Manfred Reiter, Vienna; Renate Den-Bouwmeester, Vienna, all of Austria

[73] Assignee: Immuno Aktiengesellschaft, Vienna, Austria

[21] Appl. No.: 898,131

[22] Filed: Jul. 22, 1997

Related U.S. Application Data

[62] Division of Ser. No. 653,298, May 24, 1996.

[30] Foreign Application Priority Data

Oct. 4, 1994 [DE] Germany ............................ 44 35 485
Oct. 2, 1995 [WO] WIPO ...................... PCT/EP95/03892

[51] Int. Cl.$^6$ .................................................. A61K 38/17
[52] U.S. Cl. ............................................ 514/12; 514/21
[58] Field of Search ......................................... 514/12, 21

[56] References Cited

U.S. PATENT DOCUMENTS

| | | | |
|---|---|---|---|
| 5,252,709 | 10/1993 | Burnouf et al. | 530/382 |
| 5,252,710 | 10/1993 | Dazey et al. | 530/383 |

FOREIGN PATENT DOCUMENTS

| | | |
|---|---|---|
| 0197592B1 | 10/1986 | European Pat. Off. . |
| 0 131 740 | 10/1990 | European Pat. Off. . |
| 0 416 983 | 3/1991 | European Pat. Off. . |
| 0 469 985 | 2/1992 | European Pat. Off. . |
| 0469985A1 | 2/1992 | European Pat. Off. . |
| 0 503 991 | 9/1992 | European Pat. Off. . |
| 0 519 901 | 12/1992 | European Pat. Off. . |
| 39 04 354 | 8/1990 | Germany . |
| 44 34 538 | 4/1995 | Germany . |
| 89/12065 | 2/1989 | WIPO . |
| 90/15613 | 12/1990 | WIPO . |
| 94/13329 | 6/1994 | WIPO . |

OTHER PUBLICATIONS

Wise, R. J., et al. (1991) J. Biol. Chem. 266(32), 21948–21955.
Aihara et al, "Visualization of von Willebrand Factor Multimers by Immunoenzymatic Stain Using Avidin–Biotin Peroxidase Complex", pp. 263–267, Thrombosis and Haemostasis, 1986.
Ruggeri et al, "The Complex Multimeric Composition of Factor VIII/ von Willebrand Factor", Blood, vol. 57, No. 6, Jun. 1981, pp. 1140–1143.
Samama et al, "Aprotinin Could Promote Arterial Thrombosis in Pigs: a Prospective Randomized, Blind Study", Thrombosis and Haemostasis, pp. 663–669, 1994.
Roussi, "Absence of incorporation of plasma von Willebrand factor into porcine plaelet α–granules" British Journal of Hematology, 1995, pp. 661–668.
Dorner et al, "Large–Scale Production, Purification, and Immunologic Analysis of a Vaccinia Recombinant Derived HIV–1 gp 160", Aids Vaccine Research and Clinical Trials, 1990, pp. 219–239.
Bradford, "A Rapid and Sensitive Method for the Quantification of Microgram Quantities of Protein Utilizing the Principle of Protein–Dye Binding", 1976, pp. 248–255.
Barrett et al, "Large–Scale Production and Purification of a Vaccinia Recombinant–Derived HIV–1 gp 160 and Analysis of Its Immunogenicity", Aids Research and Human Retroviruses, vol. 5, No. 2, 1989, pp. 159–171.
Weiss et al, "Quantitative Assay of a Plasma Factor Deficient in von Willebrand's Disease that is Necessary for Platelet Aggregation, Relationship to Factor VIII Procoagulant Activity and Antigen Content", The Journal of Clinical Investigation (1979) 52, 2708–2716.
Fischer et al, "Structural analysis of recombinant von Willebrand factor: identification of hetero–and homo–dimers", FEBS Letters 351, 1994, pp. 345–348.
Baillod et al, "Multimeric Analysis of von Willebrand Factor by Vertical Sodium Dodecyl Sutphate Agarose Gel Electrophoresis, Vacuum Blotting Technology and Sensitive Visualization by Alkaline Phosphatase Anti–Alkaline Phosphatase Complex", Thrombosis Research 66, pp. 745–755, 1992.
Falkner et al, "High Level Expression of Active Human Prothrombin in a Vaccina Virus Expression System", Thrombosis and Haemostasis, 1992, pp. 119–124.
Harrison, et al, "Chromatography of the VIII/vWF Complex on Dextran Sulphate Sepharose", Thrombosis Research 50, pp. 295–304, 1988.
Laemmli, "Cleavage of Structural Proteins during the Assembly of the Head of Bacteriophage T4", Nature vol. 227, pp. 680–685, 1970.
Burnouf–Radosevich et al., Vox Sang 62: 1–11 (1992).
Andrews et al., Biochemistry 28: 8326–8336 (1989).
Titani et al., Biochemistry 25: 3171–3184 (1986).
Mancuso et al., J. Biological Chemistry 264 (33): 19514–19527 (1989).
Thrombosis and Haemostatsis/Abstracts 73(6): 1160, Abstract 993 (1995).

Primary Examiner—Charles L. Patterson, Jr.
Attorney, Agent, or Firm—Foley & Lardner

[57] ABSTRACT

The invention relates to a method for isolation of highly pure von Willebrand Factor in which recombinant von Willebrand Factor (rvWF) is chromatographically purified by anion exchange chromatography on an anion exchanger of the quaternary amino type in a buffer solution comprising buffer substances and optionally salt.

The buffer solutions are preferably free of stabilizers, amino acids and other additives. According to this method, highly pure recombinant vWF can be obtained, which is free from blood plasma proteins, especially free from Factor VIII, and is physiologically active.

Further, the invention relates to a pharmaceutical preparation that contains rvWF, which is comprised of multimers with a high structural integrity

9 Claims, 1 Drawing Sheet

METHOD FOR ISOLATION OF HIGHLY PURE VON WILLEBRAND FACTOR

This application is a division of application Ser. No. 08/653,298, filed May 24, 1996, which claims section 120 priority from PCT/EP95/03892, filed Oct. 2, 1995.

The invention relates to a method for the isolation of a highly pure von Willebrand Factor (vWF). Further, the invention relates to recombinant Willebrand Factor (rvWF), which is obtainable according to the method of the invention as well as a pharmaceutical composition comprising rvWF.

In blood coagulation, the transition of liquid blood occurs in the blood clot, a gelatinous mass which brings about the sealing of injured blood vessels through thrombosis. Thereby, the transformation of soluble fibrinogen present in plasma into the fibrous, gelatinous coagulation material, fibrin, occurs in a multi-step process (so-called blood coagulation cascade) involving at least 15 different blood clotting factors characterized with roman numerals, each of which, when activated, activates the respective next inactive step.

Of the coagulation factors, calcium ions, fibrinogen and prothrombin (Factor II) constantly circulate in blood, others are activated by tissue injury or contact with collagen or phospholipids from thrombocytes (Factor XII). Numbered among the common blood-clotting factors are several serine proteases such as kallikrein, thrombin and the activated Factors VII, IX, X and XI.

The thrombocytes bind to collagen of the injured connective tissue in the presence of von Willebrand Factor (a component of the coagulation Factor VIII) through adhesion. They alter their form and develop pseudopods, and in addition to this, their outer membrane facilitates adhesion to other thrombocytes. Thereafter, they release various substances from their granula, whereby vasoconstriction as well as the accumulation and activation of other factors of plasmatic coagulation are mediated.

During normal blood coagulation, direct and indirect functions are assigned to von Willebrand Factor. It binds in a complex to Factor VIII. This complex serves to stabilize Factor VIII. This stabilized Factor VIII has then essential cofactor functions in the activation of Factor X. However, von Willebrand Factor also directly influences blood coagulation since it mediates platelet aggregation to injured vessels.

In hemophilia, blood coagulation is impaired by a deficiency in certain plasmatic blood coagulation factors. In hemophilia A, the bleeding tendency is based on a deficiency in Factor VIII, and/or a deficiency in vWF which constitutes an essential component of coagulation Factor VIII complex. Hemophilia A can be treated by replacement of the missing coagulation factor by factor concentrates from conserved blood, for example by intravenous infusion of Factor VIII, a vWF/Factor VIII complex or vWF.

There are many syndromes which can be traced back to under-or overproduction of von Willebrand Factor. Hence, an overproduction of vWF leads, for example, to an increased tendency toward thrombosis, whereas a decrease in vWF results in an increased bleeding tendency or prolonged bleeding time.

Von Willebrand Syndrome can manifest itself in several forms. All forms which may result from an absolute absence of functional vWF are distinguished by a prolonged bleeding time. A deficiency in vWF can also cause phenotypic hemophilia A because vWF is an essential component of functional Factor VIII. In these cases, the half-life of Factor VIII is decreased to such an extent that it can no longer perform its particular functions in blood-clotting.

vWF circulates in plasma in a concentration of 5–10 mg/l in the form of a non-covalent complex with Factor VIII. vWF is a glycoprotein which is formed in various cells of the human body and is later released into the circulation. Thereby, starting from a polypeptide chain with a molecular weight of approximately 220,000 (vWF monomer) in cells, vWF dimer (primary vWF dimer) is formed with a molecular weight of approximately 550,000 by formation of several disulfide bridges. Then vWF dimers with increasing molecular weights up to approximately 20 million are produced through coupling further polymers of vWF. It is suspected that especially the high molecular weight vWF fractions have an essential importance in blood coagulation.

Various methods for purifying and concentrating vWF are described in the literature, all of which use human blood plasma as a source for the von Willebrand Factor.

Structural analysis of vWF can be undertaken with high resolution electrophoretic methods. In this way, it was found by Baillod et al., Thrombosis Research 66, 745–755, 1992, that vWF multimers are separated into bands and each multimer band carries one or several satellite bands with it. This appearance is traceable back to the proteolytic degradation of vWF multimers. The simple addition of protease inhibitors to blood samples could not inhibit this degradation.

Abnormal vWF of type IIA demonstrates an altered electrophoresis pattern. As a result of the multimer analysis, it was found that in patients with von Willebrand disease of type IIA, the multimers each appear as single bands (singlets) and are not cleaved in satellite bands. This is traceable back to the fact that a protease-sensitive bond between Tyr-842 and Met-843 in the type IIA patients is possibly not cleaved. These patients demonstrate different syndromes in connection with a bleeding tendency.

A similar picture of the multimer bands for recombinant vWF is described by Fischer et al., FEBS Letters 351 (1994) 345–348. This rvWF is expressed in CHO cells and a multimer analysis was undertaken. In contrast to plasma vWF, no triplet structure was observed. Consequently, this rvWF is present as completely intact protein which is not proteolytically degraded.

However, the rvWF was not subject to any treatment methods such as a purification, virus inactivation and/or virus depletion. Consequently a pharmaceutical preparation was still not present.

The vWF preparations described in the prior art comprise vWF in a proteolytically degraded form. The stability of these preparations is thereby limited. Also, experiments to prevent proteolysis after taking a blood sample with suitable inhibitors did not lead to vWF with intact structure.

EP-A-0 503 991 describes the purification of vWF from human cryoprecipitate by three successive chromatography steps: 1. ion-exchange chromatography on DEAE (DEAE cellulose, diethylaminoethyl cellulose) Fractogel and elution of vWF by 0.15M NaCl; 2. further ion-exchange chromatography on DEAE-Fractogel and elution of the vWF by 0.17M NaCl; and 3. affinity chromatography on gelatin Sepharose®. Buffers which contained amino acids and calcium ions were used as buffer systems.

M. Burnouf-Radosevich and T. Burnouf, Vox Sang 62 (1992) 1–11 describe a similar chromatographic purification of plasma vWF by a combination of ion-exchange chromatography on DEAE-Fractogel with a gelatin Sepharose® filtration in a buffer system containing amino acids and calcium ions.

WO-A-8 912 065 describes the separation of plasma proteins from plasma cryoprecipitates through binding of the proteins on DEAE-Fractogel and through step-wise elution by increasing addition of NaCl. The method is suitable especially for isolation of Factor VIII concentrate of high purity for treating hemophilia A, as well as for isolation of concentrates of fibrinogen, vWF and fibronectin. The fractions containing vWF are preferably subjected to a second chromatography on the same anion exchanger using a buffer containing amino acids and calcium ions.

EP-A-0 416 983 describes the isolation of a vWF-Factor VIII complex from human plasma by precipitation with a combination of barium chloride and aluminum hydroxide, and subsequent anion exchange chromatography on DEAE-Fractogel.

According to Harrison et al., Thrombosis Research 50 (1988) 295–304, vWF/Factor VIII complex is purified by chromatography on dextrane sulfate agarose.

However, in the purification of vWF-Factor VIII complex according to these methods, Factor VIII:C should be obtained in higher purity.

Therefore, in the treatment of hemophilia A, continuously better purified Factor VIII:C concentrates are employed which do not contain vWF or only contain vWF in trace amounts. Therefore, such preparations are not suitable for the treatment of vWF deficiency. The need for pure von Willebrand Factor concentrate is therefore very great.

EP-A-0 469 985 and U.S. Pat. No. 5,252,710 describe a method for production of vWF from plasmacryoprecipitate which is extensively free from Factor VIII, in which vWF is separated from Factor VIII in a first purification step because vWF is not bound to the anion exchange column, but rather only to Factor VIII. Then, in a second step, the salt concentration of the material not bound to the anion exchanger is substantially decreased and vWF is bound to a second anion exchanger and then further eluted with a solution of higher ionic concentration.

DE-A-3 904 354 describes the production of a vWF concentrate from plasma cryoprecipitate by separation of vWF from Factor VIII, whereby Factor VIII, but not vWF, is bound to an ion exchanger.

U.S. Pat. No. 5,252,709 describes a method for the separation of Factor VIII, vWF, fibronectin and fibrinogen from human plasma, whereby Factor VIII, vWF and fibronectin are first bound to an ion exchanger of the DEAE type and subsequently separately eluted with increasing salt concentration from the ion exchanger.

Although these methods describe the purification of vWF with separation of Factor VIII, a low level of contamination with Factor VIII and/or with other blood plasma proteins cannot be excluded.

Additionally, all vWF concentrates which are obtained by isolation of the protein from human blood plasma or come in contact with biological material from mammals are potentially at a risk of containing pathogenic molecules from plasma donors such as, for example, viruses.

The object of the present invention relates to making available an efficient, easy and safe method for the production of highly pure von Willebrand Factor which is essentially free from other plasma proteins and especially free from Factor VIII.

A further object of the invention is to make a pharmaceutical available, which comprises a vWF whose stability is improved in comparison to previously known preparations.

This object is solved with the subject-matter of the present invention.

Subject-matter of the present invention is a method for the isolation of highly pure von Willebrand Factor in which recombinant von Willebrand Factor (rvWF) is purified by anion exchange chromatography on an anion exchanger of the quaternary amino type.

Preferably, the rvWF purified by anion exchange chromatography is further purified by affinity chromatography on immobilized heparin in a buffer solution comprising buffer substances and optionally salt.

Recombinant von Willebrand Factor is isolated from the cell-free culture filtrate of transformed, virus-free, animal cells by means of cell culture techniques.

Preferable embodiments include methods where the rvWF in the form of a concentrate is purified from cell-free culture supernatants of transformed cells. The buffer system for use with the invention is preferably free of stabilizers, amino acids and other additives.

Preferably, the anion exchange chromatography and/or affinity chromatography used according to the invention is carried out at a pH range of 6.0–8.5, and more preferably at a pH value of 7.4. The rvWF bound in on the anion exchanger or in affinity chromatography on immobilized heparin is preferably eluted by increasing the salt concentration. Preferably, the quaternary anion exchanger for use according to the invention is a Fractogel with tentacle structure, such as EMD-TMAE Fractogel.

Preferably, the rvWF is bound to the anion exchanger at a salt concentration <270 mM, and eluted at a salt concentration >270 mM and preferably at >280 mM. The anion exchange chromatography can be carried out on a carrier with heparin bound thereon, whereby AF-Heparin-Toyopearl®, Heparin EMD-Fractogel® or Heparin Sepharose Fast Flow® can be employed.

The rvWF pre-purified in anion exchange chromatography can be bound to immobilized heparin at a salt concentration <150 mM and is eluted at a salt concentration >150 mM, preferably at 200–300 mM, more preferably 160–270 mM.

The salt that can be employed according to the invention is preferably monovalent and divalent. A preferred salt is NaCl.

Further subject-matter of the present invention is a recombinant von Willebrand Factor which is free from blood plasma proteins, especially free from Factor VIII, and is obtainable according to the method of the invention. This recombinant von Willebrand Factor is physiologically active.

Further subject-matter of the present invention is the use of rvWF, in particular the rvWF obtainable according to the method of the invention, for treatment of hemophilia A, hemophilia A with a deficiency in vWF and various forms of von Willebrand disease. Further subject-matter is also the use of recombinant von Willebrand Factor for the production of a pharmaceutical composition for treating hemophilia A and hemophilia A with a deficiency in vWF. Further subject-matter is the use of rvWF obtainable according to the method of the invention for the treatment of various forms of von Willebrand's disease. Further subject-matter of the present invention is a pharmaceutical composition characterized in that it comprises nonfragmented rvWF obtainable according to the method of the invention in a physiologically acceptable carrier.

Further subject-matter is a stable preparation comprising virus-safe rvWF, which comprises multimers with high structural integrity. The multimers can be derived from a rvWF containing fraction obtainable by a chromatographic purification method, whereby the multimers are not proteolytically degraded. The rvWF can have multimer bands in the absence of satellite bands after electrophoresis analysis. The rvWF-containing fraction can obtained from a cell culture.

The preparation can be formulated to a pharmaceutical preparation for administration to patients without causing side-effects such as the formation of thrombi, thrombocyte activation or thrombocytopenia. Preferably, the preparation can remain stable in solution at room temperature for at least 50 hours. More preferably, the preparation is in a form acceptable for infusion.

The preparation can comprise salts, such as sodium chloride and calcium chloride, and amino acids such as glycine and lysine, preferably in a pH in the range of 6–8. Preferably, the preparation according is treated for inactivation and/or depletion of viruses. The pharmaceutical preparation comprising rvWF can have a multimer pattern with a singlet structure that is maintained after administration to a mammal.

The invention also pertains to a method for the treatment of hemophilia A, which comprises the steps of administering to a patient in a therapeutically effective amount of rvWF. This method also can be used to treat von Willebrand Factor deficiency.

The vWF preparation according to the invention can be added to preparations containing Factor VIII, recombinant Factor VIII or functional deletion mutants of Factor VIII.

Recombinant vWF (rvWF) is isolated from cell-free culture medium after fermentation of animal cells and purified. The culture medium used for fermentation constitutes a complex, synthetic mixture of all materials for maintaining animal cells which are customary for this purpose such as vitamins, sugars, salts, hormones, antibiotics and buffer substances, and therefore, is essentially different in all fundamental properties from the composition of human blood plasma or plasma cryoprecipitate. It was not to be predicted therefore that the method according to the invention would be outstandingly suitable for the production of highly pure von Willebrand Factor. Preferably, a recombinant vWF concentrate from cell-free culture supernatants of transformed cells is employed in the method according to the invention.

In the method according to the invention a buffer solution is preferably used for a buffer system which is comprised of buffer substances which are preferably free from stabilizers, amino acids and other additives and optionally salt, preferably sodium chloride. It is known from the prior art that stabilizers, amino acids and other additives are necessary in order to, on the one hand stabilize von Willebrand Factor and, on the other hand, to destabilize the Factor VIII-von Willebrand complex and to ease the separation of other proteins. In the method according to the invention, use of such components in the buffer can be entirely refrained from and despite this, a physiologically active recombinant von Willebrand Factor is obtained.

A buffer system free from stabilizers, amino acids and other additives is preferably used as a buffer system, such as for example, Tris-HCl/NaCl buffer, phosphate buffer and citrate buffer.

Anion exchange chromatography and/or affinity chromatography are preferably carried out in a pH range of 6.0–8.5 and particularly preferably at a pH value of 7.4.

The elution of rvWF bound to the anion exchanger in anion exchange chromatography and bound to immobilized heparin in affinity chromatography preferably occurs by increasing the salt concentration.

Fractogel® with tentacle structure, and preferably EMD-TMAE Fractogel® is used as an anion exchanger of the quaternary amino type.

Preferably, rvWF is bound to the anion exchanger at a salt concentration of <270 mM, and eluted at a salt concentration >270 mM, and preferably at >280 mM. Soluble monovalent and divalent salts are usable as salts, whereby NaCl is preferred.

Any carrier to which heparin is bound can be used for affinity chromatography. For example, AF Heparin Toyopearl® (a synthetic large pore, hydrophilic polymer based on methacrylate; Tosohaas), Heparin EMD-Fractogel® (a synthetic hydrophilic polymer based on ethyleneglycol, methacrylate and dimethacrylate; Merck) or Heparin Sepharose Fast Flow® (containing natural dextran and/or agarose derivatives; Pharmacia) have proven themselves to be well-suited.

Preferably, the rvWF pre-purified by the step of anion exchange chromatography is bound to immobilized heparin at a salt concentration of <150 mM and eluted at a salt concentration of >150 mM, preferably from 200–300 mM and more preferably 160 mM to 270 mM. Monovalent and divalent salts are usable as salts, whereby NaCl is preferred.

Based on the molecular weight of rvWF (molecular weight of 500,000 to several million) such carrier materials are preferably used in the method according to the invention in anion exchange chromatography as well as in affinity chromatography which do not impede the rvWF molecule in its diffusion and distribution within the carrier structure, such as, for example, gels with tentacle structure.

In a preferred embodiment of the method according to the invention, the cell-free culture medium is first filtered on a strong anion exchanger, whereby the rvWF is bound by the exchanger. A large pore gel with tentacle structure and with strong binding ion exchange groups of the quaternary amino type, such as for example EMD-TMAE-Fractogel® is preferably used as an ion exchanger. After removal of the accompanying proteins and impurities by means of salt-containing buffer, preferably NaCl-containing buffer, rvWF is then eluted from the ion exchanger in enriched form. In the second purification step of affinity chromatography, the eluate containing rvWF is brought into contact with an affinity carrier with covalently bound heparin, whereby rvWF binds to this carrier. After the removal of foreign substances and foreign proteins by a suitable elution substance (such as, for example, buffer substance), rvWF is eluted from the affinity carrier, preferably by means of a NaCl-containing buffer system.

A highly pure rvWF can be obtained according to the method of the invention for isolation of a highly pure von Willebrand Factor, which is free from antibodies, free from blood plasma proteins and especially free from Factor VIII, which is physiologically active and which is free from pathogenic viruses.

The highly pure rvWF is further characterized in that the portion of vWF protein to total protein is at least 800% especially at least 86%.

The highly pure rvWF obtainable according to the method of the invention can be employed in a targeted manner in the treatment of hemophilia A or hemophilia A with a deficiency in vWF as a result of its properties: that it is free from antibodies, free from plasma proteins, free from pathogenic viruses and free from Factor VIII.

Furthermore, the highly pure rvWF obtainable according to the method of the invention can be used for treatment of various forms of von Willebrand disease.

Further, according to the invention, a stable preparation is made available, which comprises rvWF consisting of multimers with a high structural integrity. This stable preparation is preferably formulated to a pharmaceutical preparation. The rvWF is so stable that it can be made available as a virus-safe preparation. The virus safety is guaranteed by method steps for treating the rvWF for inactivation of viruses and/or depletion of viruses.

A heat treatment in solution and/or in the solid state which can reliably inactivate lipid coated as well as non-lipid coated viruses is especially suited for the inactivation of viruses. For example, the preparation according to the invention is heat treated in a solid, wet condition according to EP-0 159 311. Other methods for virus inactivation also encompass a treatment with detergent or chaotropic substances, for example according to EP 0 519 901, WO 94/13329, DE 44 34 538, EP 0 131 740 and WO 90/15613.

rvWF is preferably contained in the preparation according to the present invention as a highly pure protein which is obtained by a chromatographic purification method. The chromatographic purification particularly occurs by ion exchange chromatography and/or affinity chromatography. For this, materials for anion exchange can be enlisted, among them synthetic carrier materials or carriers based on carbohydrates with ligands, such as DEAE, TMAE, QAE, Q or aminoalkyl groups and/or carriers with immobilized substances which have a specific affinity for vWF. Suitable affinity materials contain heparin for example. This purification method is suitable for large-scale isolation of rvWF.

Additionally, it is to be noted that the rvWF in the preparation according to the invention has a surprisingly sufficient resistance against proteolytic degradation such that the addition of customary stabilizers can be dispensed with. However, in exceptional cases, a suitable protease inhibitor can also be added during the production method in order to obtain the intact structure. For further support of the stability of vWF, the stable preparation, in particular the pharmaceutical preparation, can also comprise a polyalkyleneglycol such as PEG or polypropyleneglycol or glycerin in a concentration which does not precipitate rvWF and is physiologically acceptable.

According to the invention, the rvWF in the preparation has multimer bands in the absence of satellite bands after electrophoretic analysis. This corresponds to the structure of vWF, i.e. a non-fragmented, intact protein. Preferably, rvWF in the stable or pharmaceutical preparation has the entire spectrum of multimers, which is similar to native multimer distribution, especially the vWF with high molecular weight.

The stability of the preparation according to the invention is necessary above all for a liquid preparation. A solution of the preparation according to the invention is stable at room temperature, for example for at least 48 hrs., preferably for at least 72 hrs., and is storable at a temperature of 4° C. for more than 2 years. The stability is shown by an insignificant loss of activity of less than 50%, preferably less than 20%, and most preferably less than 10%, which is not substantial. Therewith, the preparation according to the invention is suitable as an infusion preparation, which can also be infused into a patient over a period of several hours without risking changing the preparation or necessitating a change in the dosage regime. With respect to the prevention of possible side-effect reactions, it is also advantageous to administer a protein with intact and stable structure.

It has emerged that the pharmaceutical preparation according to the invention can be administered to a patient without side-effect reactions such as formation of thrombi or microthrombi, thrombosis, thrombocyte activation or thrombocytopenia. This was surprising above all because rvWF in the preparation according to the invention has a similar multimer pattern to the form responsible for type IIA von Willebrand disease.

The formulation of the pharmaceutical preparation according to the invention can occur in a known and customary manner, for example, with the aid of salts and optionally amino acids, but it can also be performed in the presence of tensides. Preferably, salts such as, for example, sodium chloride or calcium chloride are used and a pH in the range of 6–8 is selected. As amino acids, glycine or lysine are preferred. Equally, a pharmaceutically suitable buffer can be chosen. As a result of the high stability of rvWF, the use of stabilizers, such as carrier proteins or inhibitors, can usually be avoided.

The preferred concentration of rvWF in the administration-ready solution is in the range of 1 to 100 units/ml. Because of the high purity of the preparation, this can also be formulated in concentrations of up to 1000 U/ml. The activity is characterized by ristocetin-mediated platelet aggregation and is given as ristocetin-cofactor activity (RCoF) (see Journal of Clinical Investigations 52, 2708–2716, 1973 for this). The normal dose for vWF lies in the range of 40–80 RCoF units/kg in intervals of 6–48 hours. As an initial dose, a higher dose of up to 200 RCoF can also be chosen.

With a biological half-life of more than 20 hrs., the half-life of rvWF after administration of the preparation according to the invention is surprisingly clearly longer than for the preparations of the prior art.

According to a further aspect of the invention, the pharmaceutical preparation comprises rvWF which maintains the multimer pattern with a singlet structure even after administration to a mammal. Therewith, a proteolytic cleavage of the singlets to satellite bands is absent.

Preferably, the stable or pharmaceutical preparation according to the invention comprises rvWF as a single essential ingredient. Therewith, this preparation can essentially comprise highly purified rvWF.

The rvWF obtainable according to the method of the invention can also be used for a stabilization of Factor VIII, of recombinantly produced Factor VIII or of functional deletion mutants of Factor VIII, whereby stabilization can be detected in vitro.

A Factor VIII preparation stabilized in this manner is not at risk, as are plasma products, of being contaminated with pathogenic viruses.

It was surprisingly found that rvWF possesses a potentially higher binding capacity for Factor VIII, and therewith, binds Factor VIII more efficiently than plasmatic vWF.

Therefore, subject-matter of the present invention is also a rvWF obtainable according to the method of the invention, characterized in that it possesses increased binding capacity for Factor VIII.

For production of the stable or pharmaceutical preparations, the highly pure recombinant von Willebrand Factor-containing fractions are preferably concentrated, and the concentrate is then further processed.

The pharmaceutical compositions can be present in a form for treatment of hemophilia A, hemophilia A with deficiency in vWF and in various forms customary and usual for administration in von Willebrand disease; preferably, they are present in a form of a preparation suitable for infusion. In the following Examples, the invention is more closely illustrated without limiting it to them.

Example 1 describes the purification of rvWF from cell-free culture medium after fermentation of transformed animal cells by anion exchange chromatography. A continuing purification by the processing step of affinity chromatography is described in Example 2.

EXAMPLE 1

Figure 1:
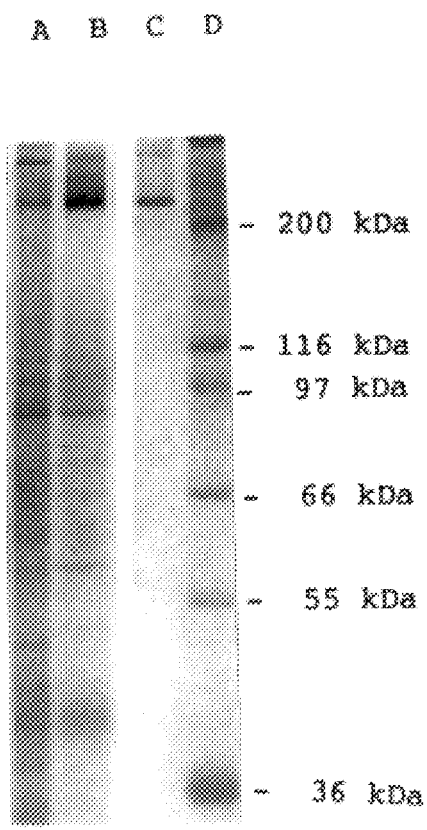
FIG. 1 represents an 8% SDS-page separation of rvWF. Lane A: culture medium; Lane B: fraction 280 mM NaCl after Fractogel; Lane C: 270 mM NaCl fraction after heparin affinity chromatography; Lane D: molecular weight marker.

Purification of rvWF from Culture Supernatants by Anion Exchange Chromatography

Recombinant vWF was isolated according to customary methods after infection of Vero cells (monkey kidney cells) with vaccinia virus in cell culture. Vero/vaccinia expression systems and cell culture conditions are described in detail in F. G. Falkner et al., Thrombosis and Haemostasis 68 (1992) 119–124; N. Barret et al., AIDS Res. 5 (1989) 159–171 and F. Donner et al., AIDS Vaccine Research and Clinical Trials, Marcel Dekker, Inc, New York (1990). The expression of rvWF occurred in a synthetic DMEM standard medium (Dulbeccol's minimal essential medium).

Recombinant vWF can also be isolated by transformation of CHO cells.

After fermentation of the transformed cells, the culture medium was separated and cells and cell fragments were removed by centrifugation. Further, smaller components, such as membrane fragments or bacteria were removed by filtration through a filter with a pore size of 0.4 µm.

770 ml cell-free culture supernatant was filtered with a flow rate of 2 ml/cm$^2$/min over a column (1.6 cm×5 cm, filled with 10 ml anion exchanger EMD-TMAE-Fractogel® (Merck)). The gel was previously equilibrated with 20 mM Tris-HCl buffer (pH 7.4). Subsequently, the column was washed with 20 mM Tris-HCl buffer (pH 7.4).

Foreign materials were removed by washing the column with buffer containing 200 mM NaCl. The rvWF was then eluted from the carrier with 280 mM NaCl in 20 mM Tris-HCl buffer (pH 7.4). Subsequently, residual material, which was possibly present, was eluted from the column with 1M NaCl. During chromatography, protein absorption was followed in a customary manner at 280 nm. After chromatography, the protein concentration was determined according to the Bradford method (M. Bradford, Anal. Biochem. 72 (1976) 248–254). The content of rvWF was determined by means of a commercial ELISA system (Boehringer Mannheim).

It was found that nearly the entire rvWF was bound to the carrier. rvWF was eluted from the anion exchanger by 0.28M NaCl. The results of the purification of rvWF on the anion exchanger are summarized in Table 1.

rvWF was enriched by 6-fold through the purification described in this Example.

TABLE 1

| Sample | Volume (ml) | Total Protein (µm/ml) | rvWF (µm/ml) | rvWF/Total Protein |
|---|---|---|---|---|
| Cell-Free Supernatant | 770 | 113 | 7.9 | 0.069 |
| Elution with 200 mM NaCl | 95 | 147 | 0.0016 | 0.00001 |
| Elution with 280 mM NaCl | 75 | 168 | 61 | 0.36 |
| Elution with 1 M NaCl | 50 | 196 | 6 | 0.03 |

EXAMPLE 2

Purification of rvWF by Affinity Chromatography rvWF obtained according to Example 1 was diluted with 20 mM Tris-HCl buffer (pH 7.4) to decrease the salt concentration (160 mM NaCl). Subsequently, the solution was filtered through a column (1.6 cm×5 cm, filled with 10 ml AF heparin Toyopearl® 650 (Tosohaas)) with a flow rate of 1 ml/cm$^2$/min. The column was previously equilibrated with 20 mM Tris-HCl buffer (pH 7.4). Non-specifically bound proteins were first removed by washing with 20 mM Tris-HCl buffer (pH 7.4). rvWF was eluted from the carrier by 270 mM NaCl in 20 mM Tris-HCl buffer (pH 7.4). Finally, residual material was washed from the column with 1M NaCl. During chromatography, protein absorption was followed in a customary manner at 280 nm. After chromatography, the protein concentration was determined by means of the Bradford method (M. Bradford, l.c.). The content of rvWF was determined by means of a commercial ELISA system (Boehringer Mannheim).

It was found that nearly the entire rvWF was bound to the column. Duging elution with 270 mM NaCl, the large part of rvWF was eluted from the column, whereas the washing with 1M NaCl contained only traces of rvWF. The results of this purification step are summarized in Table 2. The portion of rvWF protein to total protein was increased to over 86% by this purification step.

The fraction from 270 mM NaCl was more closely examined with denaturing SDS-protein gel electrophoresis (U. K. Laemmli, Nature 227, (1970) 680–685) and subsequently with a Western-Blot.

As represented in FIG. 1, the denaturing electrophoretic analysis resulted in the fact that rvWF was isolated in high purity by the purification described in Examples 1 and 2. In the product isolated in this manner, no other coagulation factors, such as for example, Factor VIII, could be detected.

TABLE 2

| Sample | Volume (ml) | Total Protein (µm/ml) | rvWF (µm/ml) | rvWF/Total Protein |
|---|---|---|---|---|
| rvWF Concentrate | 225 | 50 | 13.9 | 0.27 |
| Elution with 270 mM NaCl | 43 | 70 | 60 | 0.86 |
| Elution with 1 M NaCl | 32 | 25 | 2 | 0.08 |

The purified rvWF possesses an activity of 4.32 U/mg rvWF:Ag with respect to platelet aggregation.

EXAMPLE 3

Plasmatic vWF (p-vWF), vWF from cryoprecipitate (k-vWF) as well as recombinant vWF (r-vWF) were purified by means of heparin affinity chromatography. The different vWF preparations were examined for their binding to Factor VIII.

TABLE 3

| Sample | Stochiometry vWF:Factor VIII |
|---|---|
| rvWF | 2.0:1 |
| k-vWF | 2.6:1 |
| p-vWF | 3.0:1 |

Table 3 shows the data of the stoichiometry of vWF: Factor VIII. The data shows that r-vWF possesses an essentially higher binding capacity for Factor VIII than p-vWF.

EXAMPLE 4

Stability of recombinant von Willebrand Factor in Solution

A von Willebrand Factor preparation was prepared as described in Example 2, and formulated in a buffer containing 5 g/l $Na_3$ citrate.$2H_2O$, 2 g/l NaCl, 5 g/l glycine, 5 g/l L-lysine.HCl and 0.62 g/l $CaCl_2.2H_2O$, pH 7.0, in such a manner that the von Willebrand concentration was 10 U/ml measured by means of ristocetin mediated platelet aggregation. A solution of this type was held at 4° C., 25° C., 37° C. and 50° C. up to 70 hours. At various times, samples were taken and measured for their von Willebrand Factor activity by means of the ristocetin mediated platelet aggregation.

At 4° C. and 25° C., no change in the activity was seen in the observation time period, at 37° C. the activity remained over 80% for over 24 hours, and even at 50° C. no change in the biological activity could be established over 8 hours. Simultaneously, the antigen content was ascertained by means of ELISA. The antigen content remained the same as the starting value at all storage temperatures over the entire measurement period. The stability experiment was carried out without the customary protein stabilizers such as carrier proteins or sugar.

EXAMPLE 5

Lyophilization Behavior of Recombinant von Willebrand Factor

A recombinant von Willebrand Factor was formulated as described in Example 4, and adjusted to an activity of 10 U/ml. Then this was deep-frozen without further addition of common stabilizing agents and then subsequently reconstituted to the starting volume with water. Thereafter, the ristocetin cofactor activity was newly determined. rvWF could be reconstituted with a yield of 80%. As a comparative experiment, this was lyophilized in the presence of 0.1% human serum albumin; thereby 98% of the starting activity could be retained after reconstitution.

EXAMPLE 6

Pharmacokinetics of Multimers of Recombinant von Willebrand Factor in Pig

Von Willebrand deficient animals, such as for example the homozygous von Willebrand deficient pigs described by Roussi et al., Brit J. Haematol. 90: 661–668 1995, were used for the experiment. In this experiment a four month old female homozygous von Willebrand deficient pig weighing 37 kg was employed. This was characterized by a bleeding time of over 30 minutes measured according to the ear bleeding method of Samama et al., Thromb. Haemostas. 71: 663–669, 1994, and a von Willebrand Factor plasma level under the detection limit was determined in antigen ELISA and by the ristocetin cofactor activity. Factor VIII activity was approximately 1 U/ml measured as human Factor VIII in the 1-step clotting test, 2-step clotting test or chromogenic Factor VIII test (Immunochrom® Factor VIII:C, Immuno).

A preparation according to the invention which was isolated as described in Example 2 was injected into the pig under anesthesia at a dose of 34 RCoF U/kg body weight. Blood samples were taken at 30 min. 1 hr., 2 hrs., 3 hrs., 6 hrs., 9 hrs., 12 hrs., 24 hrs., 32 hrs., and 48 hrs. after infusion and a citrate of plasma was produced from these.

From the plasma samples, the structure of von Willebrand Factor multimers was determined by SDS-agarose gel electrophoresis in a 2% agarose gel according to the method of Ruggeri et al., Blood 57 : 1140–1143. Thereby, the von Willebrand Factor multimers were made visible by immune enzymatic staining according to Aihara et al., Thromb. Haemostas. 55 : 263–267 1986. As a primary antibody, a rabbit-anti-von Willebrand Factor-antiserum (Dakopatts, Glostrup, Denmark) was used at a dilution of 1:5,000. An alkaline phosphatase conjugated affinity purified goat-anti-rabbit-IgG H+L antibody (Axell, Accurate Chemical and Scientific Corp., NY) in a dilution of 1:1,000 served as a secondary antibody. The staining of the protein bands occurred by means of the nitroblue-tetrazolium-chloride-bromo-indolyl-phosphate substrate system.

No von Willebrand Factor could be detected in the pig before the treatment with the preparation according to the invention. After administration of the preparation, a structure of a multimer pattern comprised of singlets atypical for the native condition, which was traceable to a non-proteolytic digestion of von Willebrand Factor was demonstrated. This structural property remained unchanged over the entire observation time period, i.e. no proteolytic degradation of the preparation occurred. Commensurate with the pharmacokinetics, the preparation was successfully eliminated from the circulation. Multimers of the lowest molecular weight remained detectable up to 48 hours after infusion of the preparation.

A half-life of von Willebrand Factor according to the invention of approximately 30 hours could be calculated from the infusion experiments. As a macroscopic parameter for the normalization of the coagulation system disturbed in the deficient animal, the bleeding time was determined, which could be corrected from over 30 minutes before the infusion of von Willebrand Factor to approximately 13 minutes after infusion, whereby this effect was still detectable 32 hours after the infusion.

We claim:

1. A method for the treatment of absence or deficiency of functional von Willebrand Factor in a patient, comprising administering to the patient a therapeutically effective amount of recombinant von Willebrand that is in the form of multimers having high structural integrity.

2. The method according to claim 1, wherein the patient has von Willebrand disease.

3. The method according to claim 1, wherein the patient has hemophilia A.

4. A method for the treatment of absence or deficiency of functional von Willebrand Factor in a patient, comprising administering to the patient a therapeutically effective amount of recombinant von Willebrand that is in the form of multimers lacking satellite bands.

5. The method according to claim 4, wherein the patient has von Willebrand disease.

6. The method according to claim 4, wherein the patient has hemophilia A.

7. A method for the treatment of absence or deficiency of functional von Willebrand Factor in a patient, comprising administering to the patient a therapeutically effective amount of recombinant von Willebrand that is in the form of multimers that are free from proteolytic degradation products.

8. The method according to claim 7, wherein the patient has von Willebrand disease.

9. The method according to claim 7, wherein the patient has hemophilia A.

* * * * *